United States Patent [19]

Zardi

[11] Patent Number: 4,769,220
[45] Date of Patent: Sep. 6, 1988

[54] CONVERTER FOR HETEROGENEOUS SYNTHESIS MORE PARTICULARLY FOR AMMONIA, METHANOL AND HIGHER ALCOHOLS

[75] Inventor: Umberto Zardi, Breganzona, Switzerland

[73] Assignee: Ammonia Casale S.A., Switzerland

[21] Appl. No.: 900,757

[22] Filed: Aug. 27, 1986

[30] Foreign Application Priority Data

Sep. 13, 1985 [CH] Switzerland ............ 03949/85

[51] Int. Cl.$^4$ .............................................. C01C 1/00
[52] U.S. Cl. ................................ 422/148; 422/192; 422/198; 423/360; 423/361
[58] Field of Search .................... 422/148, 190–192, 422/198; 423/360, 361

[56] References Cited

U.S. PATENT DOCUMENTS 3,440,021 4/1969 Niedetzky et al. ............ 422/148
4,230,669 10/1980 Eagle et al. .................. 422/148
4,372,920 2/1983 Zardi .
4,405,562 9/1983 Zardi et al. .................. 422/148

Primary Examiner—Barry S. Richman
Assistant Examiner—Timothy M. McMahon
Attorney, Agent, or Firm—Ostrolenk, Faber, Gerb & Soffen

[57] ABSTRACT

A converter for heterogeneous synthesis. The converter contains a variable number of internal cartridges, each having a non-perforated external wall which forms an interspace with a internal shell wall. The converter also has a corresponding variable number of catalytic beds, each having granular catalyst. The catalyst beds are contained in a vessel having a closed bottom, an open top, and two cylindrical concentric perforated walls. The perforated walls allow for adduction and extraction of reaction gases which flow axially and radially through the catalyst beds. Heat exchangers are orientated on the same axis with the annular catalyst beds and consist of tube-bundles within a shell. Reaction gas feed tubes extend through some of the heat exchanger tube bundles.

5 Claims, 1 Drawing Sheet

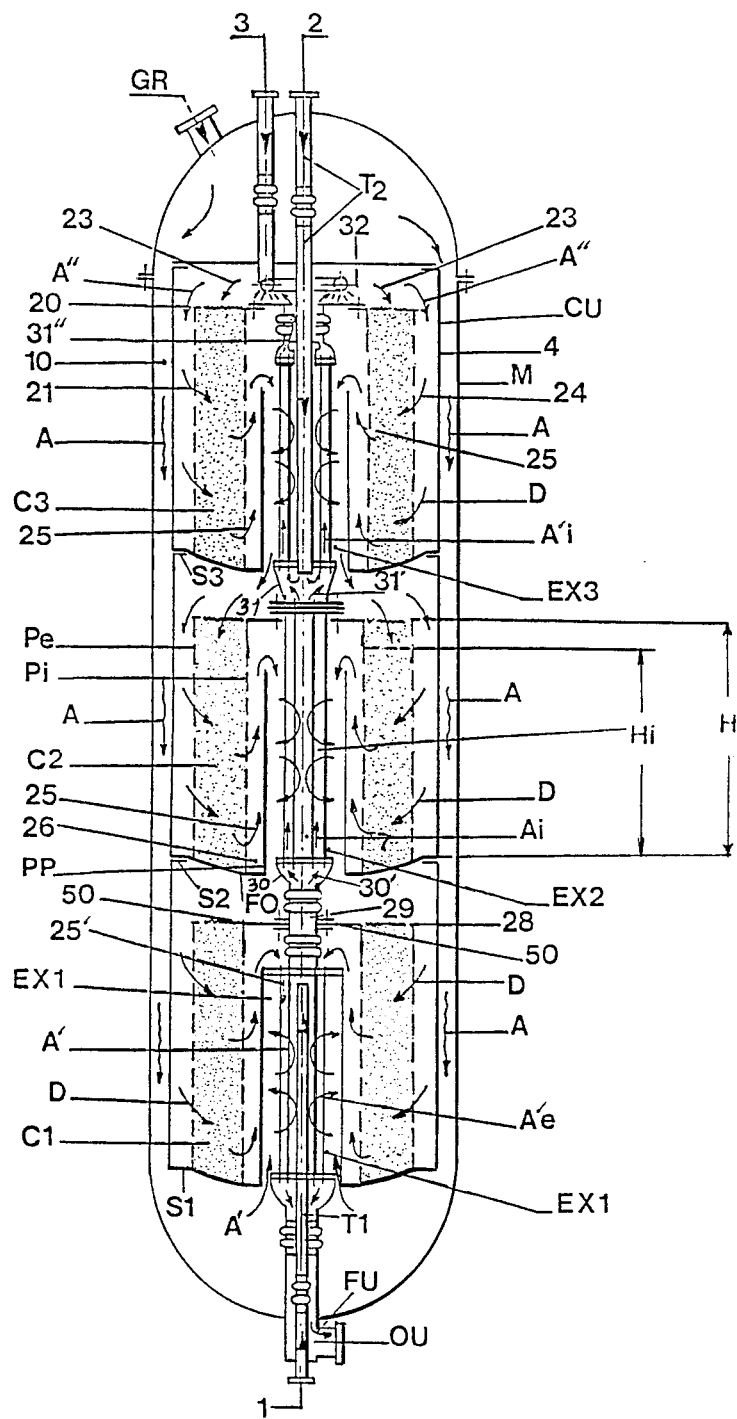

CONVERTER FOR HETEROGENEOUS SYNTHESIS MORE PARTICULARLY FOR AMMONIA, METHANOL AND HIGHER ALCOHOLS

BACKGROUND OF THE INVENTION

1. Field of the Invention

This invention relates to a heterogenous synthesis reactor. More specifically, the invention relates to a heterogenous synthesis reactor for ammonia, methanol and higher alcohols.

2. Description of the Related Art

Reactors utilizing axial and radial flow through catalyst beds are known in the art. Generally, reaction gases pass through each layer or catalytic bed in a zone with mainly axial flow and in another zone with mainly radial flow. The zone with axial radial flow acts to maintain the catalyst in the catalyst bed cartridge.

U.S. Pat. No. 4,372,920 to Zardi (the present inventor) discloses an axial-radial reactor for heterogenous synthesis using catalyst cartridges. The cartridges have an entirely perforated annular wall and a concentric annular wall with only a minor unperforated portion. Heat exchangers are located within the cartridges with feed gas flowing on the tube side only.

U.S. Pat. No. 4,405,562 to Zardi et al. discloses an axial-radial reactor for heterogenous synthesis which controls the reaction heat by the use of two catalyst cartridges. As in the U.S. Pat. No. 4,372,920 patent, the cartridges also have an entirely perforated annular wall and a concentric annular wall with only a minor unperforated portion. However, only one heat exchanger is used. Furthermore, the feed gas enters from the bottom of the reactor and flows upward to cool the external wall of the reactor's shell and collects in the central duct. The feed gas passes through the exchanger inside the exchanger's tubes, emerging pre-heated in the free zone over the top layer of the catalyst bed where it is mixed with fresh gas.

The reactors of the prior art discussed above provide for temperature control between each bed by means of direct injection of fresh gas or the use of heat exchangers.

Direct injection of fresh gas is achieved by direct admixture between feed gas at a lower temperature and hot gas coming out from each bed of the reactors. However, the conversion efficiency of the reactors is poor because the admixture of the feed gas and the hot gases is not precisely controllable. Also, the use of heat exchangers does not provide for precise temperature control.

SUMMARY OF THE INVENTION

An object of the present invention is therefore to provide a heterogeneous synthesis reactor with increased efficiency.

Another object of the invention is to provide a heterogeneous synthesis reactor with improved temperature control.

A further of the present invention is to provide a heterogeneous synthesis reactor with improved conversion efficiency.

The present invention achieves the foregoing objectives by providing for the injection of fresh gas at a lower temperature at specific locations in the reactor in conjunction with the use of a plurality of catalyst beds and heat exchangers.

DESCRIPTION OF THE DRAWINGS

The drawing is an illustration of a reactor according to the present invention.

DETAILED DESCRIPTION OF THE INVENTION

Referring first to the drawing, a heterogeneous synthesis reactor M of the present invention is illustrated generally as 100. Reactor 100 contains a variable amount of cartridges CU. The cartridges CU carry the catalyst, and provide for gas distribution. Cartridges CU are annular in shape and contain a cylindrical closed wall 4. The cartridges CU, are attached by joint elements S1, S2 and S3.

Cartridge CU has an internal perforated wall Pi, and an external perforated wall Pe. These walls are perforated along the lower major zone Hi of their height H. Each cartridge CU also includes a slightly smaller diameter non-perforated wall PP which, together with the perforated wall Pi, forms an outlet collector 26 for each catalyst bed. Cartridge CU also includes a closed bottom FO but has an open top 50.

Within the annularly shaped cartridge containing catalysts C, vertical tube-bundle exchangers EX1, EX2 and EX3 are located.

In operation, fresh reaction gas is introduced into the reactor through inlet GR. The reaction gas flows downward from the top of the reactor to the bottom of the reactor through interspace 10 as illustrated by A. Upon reaching the bottom of the reactor, reaction gas flows upward through the first heat exchanger EX1, as illustrated by A'. In the first heat exchanger EX1, the reaction gas flows outside the tubes of the heat exchanger EX1. Upward flow A' is pre-heated in heat exchanger EX1 by counter-current flow of reacted gas A'e flowing inside the tubes of heat exchanger EX1 as seen by arrow 25'.

Upon exiting heat exchanger EX1, reaction gas A' is mixed with fresh exchange gas introduced through inlet 1. Specificaly, the reaction gas exits heat exchanger EX1 through pipe 29 and flows to mixing body 30 where reaction gas is mixed with fresh exchange gas from inlet 1 through tube T1. The resulting mixture of gases 30' then flows upward through heat exchanger EX2 inside the tubes of the heat exchanger as seen by arrow Ai. Reacted gas 25 flows outside the tubes of the heat exchanger EX2 such as to further heat the reaction gas and fresh exchange gas mixture 30' in heat exchanger EX2.

The mixture of gases 30' then exits heat exchanger EX2 and is mixed further in the closed mixing body 31 with fresh exchange gas entering the reactor through inlet 2, and central tube T2. The mixture of gases 31' then flows inside the tubes of heat exchanger EX3 as shown by arrow A'i, to the top of the reactor. At the top of the reactor, gas mixture 31' is further mixed with fresh exchange gases entering through inlet 3 and dispersed in the open space of the reactor 32 by torroidal shaped element 33 to become gas mixture A".

At the top of the reactor, the mixture of reaction gases and fresh exchange gases descends through the reactor through the catalysts bed, C1. A minor amount of the gases 23 flows axially through the catalyst bed by entering the top of the catalyst bed. However, the majority 25 of the gas flows over the catalyst bed edge 28 and enters the catalyst bed from the side through the perforated walls Pe. The gas mixture travels through the catalyst bed radially as seen by arrows 24, D, and 21, becoming reacted gas 25, which then exits the catalyst bed through the inner perforated wall Pi. The reacted gas 25 is collected in collector 26, which causes the reacted gas flow 25 to flow upward to the top of exchanger EX3. The reacted gas 25 then flows outside the tubes of heat exchanger EX3.

The identical process is repeated in catalyst bed C2 and heat exchanger EX2.

When the reacted gases reach heat exchanger EX1, the reacted gases 25 are flowed inside the tubes of heat exchanger EX1 with the reaction gases flowed outside the tubes.

The reacted gases 25 are then collected in central outlet FU and exit the reactor through outlet OU.

Although the present invention has been described in connection with the preferred embodiments thereof, many other variations and modifications will now become apparent to those skilled in the art without departing from the scope of the invention. It is preferred, therefore, that the present invention be limited not by the specific disclosure herein, but only by the appended claims.

I claim:

1. In a converter for heterogeneous synthesis, and more particularly for synthesis of ammonia, methanol and higher alcohols having:
   a top, a bottom and an external shell;
   upper, intermediate and lower internal cartridges disposed from top to bottom in said converter, each having:
   (i) a non-perforated external wall defining an annular space between said exterior wall and said external shell;
   (ii) an annularly shaped catalyst bed of granular catalyst, said catalyst bed having a first zone in which gas flows radially and a second zone in which gas flows axially;
   (iii) inner and outer cylindrically concentric perforated walls;
   (iv) means for inlet of reaction gases;
   (v) means for outlet of reacted gases and;
   (vi) a heat exchanger having a top comprising a plurality of tubes contained in a shell, orientated axially at the center of said catalytic bed,
   the improvement comprising:
   conduit means for channeling said reaction gas to flow from said top to said bottom through said annular space between said shell and said upper, intermediate and lower internal cartridges;
   means for directing said reaction gas channeled to said bottom to flow through the heat exchanger of the cartridge disposed at the bottom of said converter on the outside of the tubes of said heat exchanger, and means for directing said reacted gas to flow through the heat exchanger of the cartridge at the bottom of said converter on the inside of said tubes;
   means for directing said reaction gas to flow through the heat exchangers of the remaining cartridges on the inside of said tubes, and means for directing said reacted gas to flow through the heat exchangers of the remaining cartridges on the outside of the tubes;
   the top of said intermediate and lower heat exchangers being provided with means for mixing said reaction gas with fresh exchange gas comprising mixing bowls; and,
   three inlet tubes for feed gas, two of said inlet tubes passing centrally through two of said inner concentric perforated walls, and wherein said two inlet tubes are introduced into said mixing bowls disposed at the top of said intermediate and lower heat exchangers.

2. A converter as claimed in claim 1, wherein said cartridges have at least one internal wall with a non-perforated minor zone, said internal wall forming an interspace with a non-perforated wall such that reacted gases are collected in said interspace and the third inlet tube discharges gas into an open region at the top of said converter.

3. A converter as claimed in claim 1, wherein at least one of said inner and outer cylindrically concentric perforated walls of each cartridge has a non-perforated minor zone that defines a region of axial flow in said catalytic bed, the reaction gas flowing axially and radially through said catalytic beds.

4. A converter as claimed in claim 3, further comprising an interspace between said inner concentric perforated wall having the non-perforated minor zone, and a further non-perforated concentric wall axially disposed within said inner concentric perforated wall, said further non-perforated concentric wall having a length shorter than said inner concentric perforated wall to allow for flow of gas over said further non-perforated concentric wall.

5. A process for the reaction of gases in a reactor having a top and bottom, comprising the steps of:
   feeding reaction gas into the top of said reactor and passing said reaction gas downward in said reactor;
   flowing said reaction gas back to the top of said reactor through a lower, an intermediate, and an upper heat exchanger, each heat exchanger comprising a plurality of tubes contained in a shell, each heat exchanger being located respectively within a lower, an intermediate, and an upper annularly shaped catalyst bed located within said reactor;
   flowing said reaction gas through said lower heat exchanger outside of the tubes of said heat exchanger;
   mixing said reaction gas exiting said lower heat exchanger with fresh exchange gas introduction via a tube extending upward from the bottom of the reactor through said lower heat exchanger;
   flowing said reaction gas through said intermediate heat exchanger and said upper heat exchanger inside of the tubes of said intermediate and upper heat exchangers;
   mixing said reaction gas exiting said intermediate heat exchanger with fresh gas introduced through a tube extending downward through said upper heat exchanger, and mixing said reaction gas exiting said upper heat exchanger with fresh exchange gas introduced at the top of said reactor;
   flowing said reaction gas exiting said upper heat exchanger axially and radially through an upper catalyst bed where the reaction gas is reacted to become reacted gas;
   flowing said reacted gas through said upper heat exchanger outside of the tubes of said upper heat exchanger;
   flowing said reacted gas, axially and radially through said intermediate catalyst bed;

flowing said reacted gas exiting said intermediate catalyst bed through said intermediate heat exchanger outside of the tubes of said intermediate heat exchanger;

flowing said reacted gas axially and radially through said lower catayst bed;

flowing said reacted gas exiting said lower catalyst bed through said lower heat exchanger inside of tubes of said lower heat exchanger; and collecting said reacted gas in an outlet at the reactor bottom.

* * * * *